(12) United States Patent
Towe et al.

(10) Patent No.: US 11,464,989 B2
(45) Date of Patent: Oct. 11, 2022

(54) CONTROLLED STIMULATION DELIVERY FROM NEUROSTIMULATOR

(71) Applicant: Arizona Board of Regents on behalf of Arizona State University, Scottsdale, AZ (US)

(72) Inventors: Bruce C. Towe, Mesa, AZ (US); Daniel Gulick, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 389 days.

(21) Appl. No.: 16/515,460

(22) Filed: Jul. 18, 2019

(65) Prior Publication Data
US 2019/0336777 A1 Nov. 7, 2019

Related U.S. Application Data

(63) Continuation of application No. 15/226,775, filed on Aug. 2, 2016, now Pat. No. 10,441,803, which is a
(Continued)

(51) Int. Cl.
*A61N 1/378* (2006.01)
*A61N 5/04* (2006.01)
(Continued)

(52) U.S. Cl.
CPC ....... *A61N 1/3787* (2013.01); *A61N 1/36125* (2013.01); *A61N 1/36175* (2013.01); *A61N 1/37205* (2013.01); *A61N 5/045* (2013.01)

(58) Field of Classification Search
CPC .............. A61N 1/3787; A61N 1/36125; A61N 1/36175; A61N 1/05; A61N 1/37;
(Continued)

(56) References Cited

U.S. PATENT DOCUMENTS

| 3,735,756 A | 5/1973 | Richards et al. .......... 128/24 A |
| 4,935,345 A | 6/1990 | Guilbeau et al. |

(Continued)

FOREIGN PATENT DOCUMENTS

| WO | WO/1996/020754 | 7/1996 |
| WO | 2004016315 A1 | 2/2004 |

(Continued)

OTHER PUBLICATIONS

DeHennis et al., A Double-Sided Single-Chip Wireless Pressure Sensor, The 15th IEEE International Conference on Micro Electro Mechanical Systems, pp. 252-255, 2002.
(Continued)

*Primary Examiner* — Deborah L Malamud
(74) *Attorney, Agent, or Firm* — Lewis Roca Rothgerber Christie LLP

(57) ABSTRACT

A system for providing neurostimulation includes an external device ("external exciter") and an implanted device. The external exciter includes an energy source which inductively powers the implanted device. Examples of such external exciters include devices having at least one of: ultrasonic transducers, Radio Frequency (RF) transmitters, and solar cells. The implanted device includes circuitry that limits its maximum energy output to a predetermined saturation threshold such that excess stimulation from the external exciter does not raise the output of the implanted device beyond the saturation threshold. The output signal of the external exciter is then pulse-width modulated in order to produce a desired amount of output stimulation from the implanted device to stimulate the bioelectrically excitable tissue at a desired level.

24 Claims, 12 Drawing Sheets

Related U.S. Application Data continuation of application No. 14/357,901, filed as application No. PCT/US2012/064820 on Nov. 13, 2012, now Pat. No. 9,446,255.

(60) Provisional application No. 61/559,096, filed on Nov. 13, 2011.

(51) Int. Cl.
*A61N 1/36* (2006.01)
*A61N 1/372* (2006.01)

(58) Field of Classification Search
CPC ...... A61N 1/3718; A61N 1/378; A61N 1/025; A61N 1/3605; A61N 1/37223; A61B 2560/0214; Y10T 29/49018
See application file for complete search history.

(56) References Cited

U.S. PATENT DOCUMENTS

| | | | |
|---|---|---|---|
| 5,807,397 A | 9/1998 | Barreras et al. | 607/61 |
| 5,957,851 A | 9/1999 | Hossack | 600/459 |
| 6,047,214 A * | 4/2000 | Mueller | H02J 50/12 |
| | | | 607/60 |
| 6,231,516 B1 | 5/2001 | Keilman et al. | 600/485 |
| 6,456,883 B1 | 9/2002 | Torgerson et al. | 607/34 |
| 6,562,033 B2 | 5/2003 | Shah et al. | 606/41 |
| 7,702,395 B2 | 4/2010 | Towe et al. | |
| 8,282,561 B2 | 10/2012 | Towe | |
| 8,340,773 B2 | 12/2012 | Towe et al. | |
| 8,369,956 B2 | 2/2013 | Towe et al. | |
| 8,560,060 B2 | 10/2013 | Donofrio | |
| 8,626,303 B2 | 1/2014 | Towe et al. | |
| 8,725,270 B2 | 5/2014 | Towe | |
| 8,774,928 B2 | 7/2014 | Towe et al. | 607/48 |
| 8,909,343 B2 | 12/2014 | Towe | |
| 9,457,196 B2 | 10/2016 | Towe et al. | |
| 9,555,258 B2 | 1/2017 | Towe et al. | |
| 9,693,708 B2 | 7/2017 | Towe | |
| 9,700,712 B2 | 7/2017 | Towe | |
| 10,016,612 B2 | 7/2018 | Towe et al. | |
| 10,022,566 B2 | 7/2018 | Towe | |
| 10,252,085 B2 | 4/2019 | Towe et al. | |
| 2005/0055073 A1 | 3/2005 | Weber | 607/99 |
| 2006/0136007 A1 | 6/2006 | Mickle et al. | 607/45 |
| 2007/0142867 A1 | 6/2007 | Kim et al. | 607/18 |
| 2008/0188730 A1 | 8/2008 | Sweeney et al. | 600/345 |
| 2009/0326611 A1 * | 12/2009 | Gillbe | A61N 1/3787 |
| | | | 607/61 |
| 2010/0114258 A1 | 5/2010 | Donofrio et al. | 607/63 |
| 2010/0152817 A1 | 6/2010 | Gillbe | |
| 2012/0041310 A1 | 2/2012 | Towe | |
| 2013/0096435 A1 | 4/2013 | Towe | |
| 2015/0148710 A1 | 5/2015 | Towe et al. | |
| 2015/0306429 A1 | 10/2015 | Towe et al. | |
| 2017/0095198 A1 | 4/2017 | Towe | |
| 2017/0258363 A1 | 9/2017 | Towe | |
| 2017/0274200 A1 | 9/2017 | Towe | |
| 2018/0093112 A1 | 4/2018 | Towe et al. | |
| 2019/0247668 A1 | 8/2019 | Towe et al. | |
| 2019/0282835 A1 | 9/2019 | Towe et al. | |
| 2020/0061368 A1 | 2/2020 | Towe et al. | |

FOREIGN PATENT DOCUMENTS

| | | |
|---|---|---|
| WO | WO/2004/105583 | 12/2004 |
| WO | 2008137703 A1 | 11/2008 |
| WO | 2010027963 A1 | 3/2010 |
| WO | WO/2010/135634 | 11/2010 |
| WO | 2011156495 A2 | 12/2011 |
| WO | 2012030962 A2 | 3/2012 |
| WO | 2013169363 A2 | 11/2013 |
| WO | 2013176744 A1 | 11/2013 |
| WO | 2014093332 A1 | 6/2014 |
| WO | 2015069446 A1 | 5/2015 |
| WO | 2015142842 A2 | 9/2015 |

OTHER PUBLICATIONS

Harpster et al., A passive wireless integrated humidity sensor. Sensors Actuators A: Physical, 95(2-3):100-07, 2002.

Heetderks, W. "RF Powering of Millimeter- and Submillimeter-Sized Neural Prosthetic Implants" IEEE Transactions on Biomedical Engineering, May 1988, vol. 35, No. 5, 323.

International Preliminary Report on Patentability in International Application No. PCT/US2012/064820 dated May 22, 2014.

Lindsey et al., A new technique for transmission of signal from implantable transducers. IEEE Trans. Biomed. Engineering, 45(5):614-619, 1998.

Matthaei, "A Study of the Optimum Design of Wide-Band Parametric Amplifiers and Up converters Up Converters", IRE Transactions on Microwave Theory Tech. vol. MTT-10, pp. 23-28 Jan. 1961.

Mingui et al,; Data communication between brain implants and computer. IEEE Transactions on Neural Systems and Rehabilitation Engineering, 11(2):189-192, 2003.

Mohseni, K. Najafi, S. J. Eliades, and X. Wang, "Wireless Multichannel Biopotential Recording Using An Integrated Fm Telemetry Circuit", Ieee Transactions On Neural Systems and Rehabilitation Engineering, vol. 13, No. 3, Sep. 2005.

Sard, B. Peyton, S.Okwit, "A positive resistnace up-converter for ultra-low noise amplification" IEEEE Trans. Micro Theory Techvol. 14, pp. 608-618, Dec. 1966.

Search Report and Written Opinion in International Application No. PCT/US2012/064820 dated Feb. 26, 2014.

Takahata, et al., "Stentenna: A MicroMachined Antenna Stent for Wireless Monitoring of Implantable Microsensors." Proceedings of the 25th Annual International Conference of the IEEE EMBS. 3360-3, 2003.

Towe, Passive Backscatter Biotelemetry for Neural Interfacing, 3rd International IEEE/EMBS Conf., 144-147, 2007.

Towe, Passive Biotelemetry by Frequency Keying, IEEE Trans. Biomed. Engineering, BME-33:10, 1986.

Wise et al.,Wireless Implantable Microsystems: High-Density Electronic Interfaces to the Nervous System. IEEE Trans. Biomed. Engineering, 92(1):76-97, 2004.

\* cited by examiner

CONTROLLED STIMULATION DELIVERY FROM NEUROSTIMULATOR

PRIORITY CLAIM

This is a continuation of U.S. application Ser. No. 14/357,901 filed May 13, 2014, claiming priority to PCT Patent Application PCT/US2012/064820 filed Nov. 13, 2012 and U.S. Provisional Patent Application Ser. No. 61/559,096 filed Nov. 13, 2011. The above-referenced disclosures are in incorporated herein by; reference in their entirety.

BACKGROUND OF THE INVENTION

Field of the Invention

Embodiments generally relate to apparatuses, devices, kits, systems, assemblies and methods for neurostimulation and more specifically for control of electrical stimulation from an implanted neurostimulator, and more particularly, apparatuses, devices, kits, systems, assemblies and methods for external control of electrical stimulation output from an implanted neurostimulator to stimulate bioelectrically excitable tissue.

Description of Related Art

Nerves in higher biological organisms, such as humans or animals, are bundles of long, excitable cells that can extend to meter-order lengths. Cells are referred to as excitable when they are capable of responding to various electric, chemical, optical, or mechanical stimuli by changing their cell transmembrane potential (TMP). A cell's TMP is a measure of the potential difference across the cell's membrane. A TMP can be created due to different concentrations of ions on either side of the membrane. Cells typically maintain lower concentrations of ions inside the cell than the concentration of ions outside the cell to prevent the cell from swelling due to osmosis. Therefore, cells typically have a TMP or are depolarized.

A localized stimulus to an excitable cell, known as an action potential, can affect the cell's TMP. The reduction in TMP causes the cell's membrane to allow sodium ions to rush into the cell, which further reduces the cell's TMP. The reduction of the TMP is known as depolarization. A cell without TMP will swell due to osmosis, therefore, shortly after the sodium inrush the cell expels potassium through the cell membrane. Reducing the potassium concentration inside decreases charge within the cell and increases the TMP. The process of restoring a cell's TMP is known as repolarization.

During the time when the cell is depolarized, it cannot be restimulated by another action potential. This interval is known as the cell's absolute refractory period. The cell's relative refractory period is the interval from partial to complete repolarization. During this time, the cell can be restimulated, but a higher stimulus is required to produce an action potential event, and the response of the excitable cell is lower in magnitude.

Nerve cells are a particular type of excitable cell that are typically characterized by a cell body from which extend dendrites and an axon. The long axon is coated in myelin sheaths and axon terminals extend from the end of the axon. When the nerve cell is stimulated, a depolarization wave travels down the axon to the axon terminals. The axon terminals respond to the depolarization wave by releasing specialized chemicals known as neurotransmitters. The neurotransmitters bind to receptors in the dendrites of adjacent nerve cells and depending on the type of receptor that is activated, will either excite or inhibit the generation of an action potential in the adjacent cell. In this way, signals are passed from one nerve cell to another and enable pulses to be carried along nerve fibers.

Generally, electric currents applied to tissue affect the membranes of excitable cells, causing a depolarizing effect that can lead to a cell action event that depends on the cell type and biological function. Neurostimulation is a term used to describe the artificial excitation or inhibition of nerve cells. Here, small electric currents are applied to excitable tissues of the body such as nerve, muscle, heart, and brain for stimulation and/or control of their functions.

Neurostimulation is thought to be desirable as either a tool for simulating nerve function or for inhibiting the flow of information to the brain (e.g. blocking pain impulses). The ability to selectively stimulate specific nerve fibrils in a complex nerve bundle containing thousands of fibrils is a long-sought capability in biomedical research. Advances in biomedical research have enabled neurostimulators that are currently used in the treatment of many medical disorders including the treatment of pain, epilepsy, Parkinson's disorder, pacing and cardiac arrhythmias, neuralgias, and restoration of lost muscle function, and in brain-machine interfaces.

Neurostimulators are electric pulse generators typically powered by batteries and implanted within the body and which then supply electrical currents to tissues by way of surgically implanted electrical lead wires. Commercial versions of these pulse generators presently have a volume on the order of many cubic centimeters and weight on the order of tens of grams requiring surgery for their implantation, making their use somewhat uncomfortable and cosmetically unattractive. The batteries of these devices need to be either periodically recharged or the whole device explanted and replaced when the batteries wear down.

There has been a trend in the technology to replace large battery powered devices with smaller implanted neurostimulators that do not have batteries but are instead powered inductively through the skin. This reduces the size and bulk of the implanted device. Further reductions in size and bulk are highly desired to reduce the trauma of surgical implantations and to increase patient comfort by reduction in the device's weight.

SUMMARY

In certain embodiments, a system for stimulating an electrode configured to deliver an electrical stimulation to tissue of a subject includes an implantable device and an exciter. The implantable device includes an energy acquisition device; a voltage limiting device connected to the energy acquisition device; and an electrode connected to the voltage limited device. The exciter is configured to radiate a pulse width modulated excitation signal to the energy acquisition device of the implantable device.

In certain embodiments, an implantable device for delivering an electrical stimulation to tissue of a subject includes an energy acquisition device, a voltage limiting device connected to the energy acquisition device, and an electrode connected to the voltage limiting device. The energy acquisition device is configured to receive a pulse width modulated excitation signal and generate an output voltage. The voltage limiting device is configured to limit an amount of energy transmitted by the implantable device. The electrode is configured to deliver the electrical stimulation to the tissue of the subject.

In certain embodiments, a method of stimulating an electrode configured to deliver an electrical stimulation to tissue of a subject includes placing an exciter in spatial proximity to an implantable device and providing electronic instructions to an exciter to radiate a pulse-width modulated output excitation signal directed at the implantable device. The implantable device includes an energy acquisition device; a voltage limiting device connected to the energy acquisition device; and an electrode connected to the voltage limited device.

BRIEF DESCRIPTION OF THE DRAWINGS

The invention will be better understood from a reading of the following detailed description taken in conjunction with the drawings in which like reference designators are used to designate like elements, and in which.

DESCRIPTION

The invention is described in preferred embodiments in the following description with reference to the FIGs., in which like numbers represent the same or similar elements. Reference throughout this specification to "one embodiment," "an embodiment," "an implementation," or similar language means that a particular feature, structure, or characteristic described in connection with the embodiment is included in at least one embodiment of the present invention. Thus, appearances of the phrases "in one embodiment," "in an embodiment," "in certain embodiments," "in certain implementations," and similar language throughout this specification may, but do not necessarily, all refer to the same embodiment. It is noted that, as used in this description, the singular forms "a," "an," and, "the" include plural referents unless the context clearly dictates otherwise.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention in detail.

Figure 1:
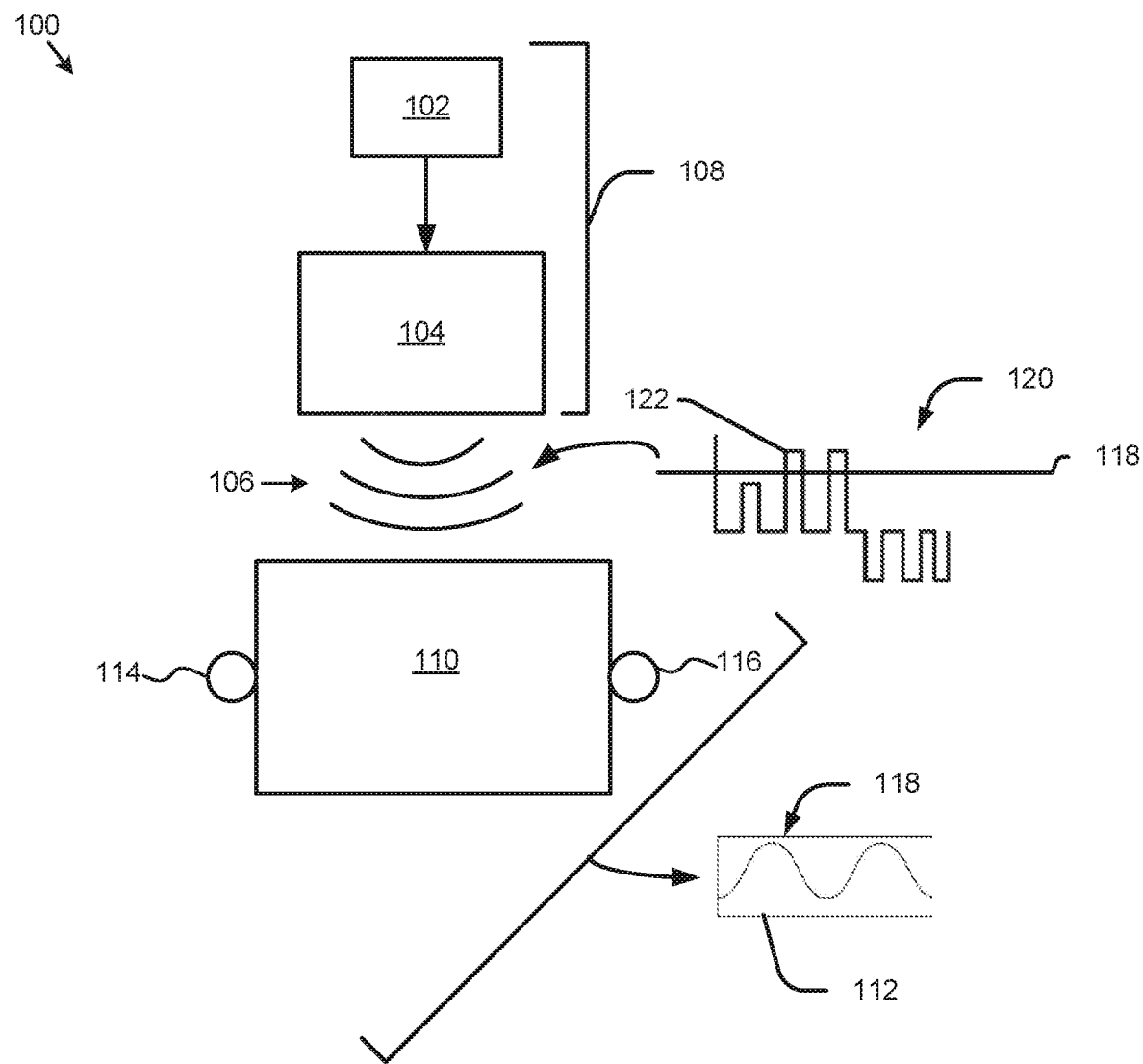
FIG. 1 is a schematic block diagram showing a neurostimulation system.

Referring to FIG. 1, a schematic block diagram illustrates a system 100 for providing neurostimulation to bioelectrically excitable tissue (not shown), such as a nerve, spinal cord, brain, muscle, heart tissue, or tissues of other organs. System 100 includes an external device ("exciter") 108 and an implantable device 110. The exciter 108 includes a power source driver 102 that is coupled to a transmitter 104 and is configured to cause the transmitter 104 to emit an output signal 106 directed towards the implantable device 110. When placed in spatial proximity to one another, the exciter 108 is communicatively coupled to the implantable device 110 such that energy radiated by the exciter 108 stimulates the implantable device 110, which may be implanted in biological tissue. The electrical currents within the implantable device 110 are applied to tissue through small round electrodes placed at the ends (114 and 116, respectively) of the implantable device 110, and may be made of platinum. Other geometries are possible and may be useful such as where the devices are made part of nerve cuffs or parts of a silicone custom molded part with electrodes in positions that match the electrophysiological requirements for placement in tissue. The implantable device 110 includes circuitry that limits its maximum energy output stimulation 112 to a predetermined saturation threshold 118 such that excess stimulation from the exciter 108 (compare element 122 with element 118 of FIG. 1) does not raise the output of the implantable device 110 beyond the saturation threshold 118. In certain embodiments, the output signal 106 of the exciter 108, in turn, is pulse-width modulated 120 in order to produce a desired amount of output stimulation 112 from the implantable device 110 to stimulate the bioelectrically excitable tissue at a desired level.

Example exciters 108 include devices that radiate energy in the form of at least one of: ultrasound, radio frequency (RF), and light energy (that may be converted to electrical energy by solar cells (p-n junction diodes as energy receivers)). In certain embodiments, the exciter 108 includes an RF transmitter that radiates RF energy. Here, the transmitter 104 is a radio frequency transmitter that is coupled to a diplexer that acts as an antenna and is configured to emit the output signal 106 as a radio frequency output. The neurostimulation waveform generated by the implant is determined by the amplitude, pulse duration, and pulse repetition rate that characterizes the transmitted energy. Thus there is a one to one correspondence between the applied energy pulse from outside the body to the electrical pulse generated by the implanted device. This approach has the advantage of great simplicity since there is no complex integrated circuit pulse generator required in the implant and that power for the function of an typical silicon integrated circuit device is not required. All of the harvested energy is used to power the electrical output of the implant.

In each case the exciter creates a short duration RF pulse whose duration equals the desired neurostimulation pulse width of the implant. This induced electrical pulse is typically on the order of fifty microseconds to tens of milliseconds as needed for the neurostimulation application.

The radio frequency transmitter controls the radio frequency output, such as controlling its frequency, amplitude (intensity), and/or modulation. In one implementation the radio frequency transmitter is configured to emit a radio frequency output in the microwave frequency range (e.g., ISM bands, or 1 to 40 gigahertz "GHz"); at approximately 915 megahertz (MHz); or at 2.45 GHz, for example. In certain embodiments, filtering is employed so that the second and higher order harmonics are suppressed at least 80 db below the transmitted signal and preferably 100 db. This is achieved by the use of engineering design of the power amplifier stages and through the use of passive low-pass filters.

In certain embodiments, the exciter 108 radiates ultrasound energy. Here, the power source is the ultrasound driver 102 that is coupled to an ultrasound transmitter 104. The ultrasound driver 102 is configured to cause the ultrasound transmitter 104 to emit the output signal 106 as an ultrasound output. In some embodiments, the ultrasound output varies in frequency, amplitude, and duration. For example, the ultrasound transmitter (transmitter 104) can be configured to emit ultrasound waves at a frequency between 20 kilahertz (kHz) to 100 MHz, such as 200 kHz to 2 MHz or higher. In some embodiments, the ultrasound transmitter creates an output at a frequency between 100 KHz to 1 MHz. Further, the ultrasound output amplitude is variable such as by making the ultrasound stronger or weaker.

In certain embodiments, the exciter 108 is configured to radiate energy in the form of a pulse-width modulated (PWM) signal 120. The duty cycle of the PWM signal is adjusted to control a total amount of energy radiated by exciter 108. Energy transmitted from exciter 108 is received by implantable device 110. By reducing the duty cycle of the PWM stimulation signal transmitted by exciter 108, the amount of energy received by implantable device 110 is controlled. For example, in the implementations where the exciter emits ultrasonic energy, a 1 MHz sine wave is outputted from the ultrasound transmitter 104 for a duration of 100 microseconds at a particular amplitude and then turned off (i.e. reduced to an amplitude at or near zero). In some embodiments, the output signal 106 is pulsed for a duration between 1 microsecond and 20 milliseconds. Therefore, an example of a pulsed output is a 1 MHz signal that lasts for 1 millisecond 100 times every second.

Implantable device 110 includes an energy acquisition system configured to receive energy transmitted by exciter 108 and use that energy to induce an electrical output 112, such as a current or a voltage. Implantable neurostimulators of this type provide an advantage of reduction in size to the point where the implantable device 110 is implantable through a syringe needle or in a minimally invasive way. For example, in certain embodiments, the size of the implantable device 110 is about 1 mm in diameter and 1 cm in length. Here, the small size of the implantable device 110 is largely based on the relative simplicity of electrical circuitry and by the methods used to gather and transform energy supplied from the exciter 108 located outside of the body.

To illustrate, where exciter 108 emits ultrasonic energy, the energy acquisition system comprises a piezoelectric material (such as PZT) that generates a voltage when impinged upon by the ultrasonic energy. Here, the output signal 106 of exciter 108 is an ultrasound output that excites the piezoelectric within the implanted device 110. In some embodiments, implanted device 110 includes a piezoelectric material and a semiconductor diode, such as Schottky diode or an Avago HSMS955 zero-bias diode that rectifies the ac signal from the piezoelectric material to obtain a monophasic waveform that is effective in neurostimulation. High frequency ac electrical signals alone may not be effective in neurostimulation.

In cases where exciter 108 emits RF energy, the implantable device 110 includes an RF dipole (e.g., a 1-2 cm long dipole antenna) configured to absorb the RF energy and generate a corresponding voltage, for example. The dipole captures the electric field in tissue induced by the transmitter 104, such as a high frequency (GHz range) RF transmitter, and then uses the diode to rectify the energy making it suited to neurostimulation of the tissue in proximity to implantable device 110.

Consequently, the neurostimulation waveform generated by the implantable device 110 is determined by the amplitude, pulse duration, and pulse repetition rate that characterizes the transmitted energy. Thus, there is a one-to-one correspondence between the applied energy pulse from outside the body to the electrical pulse generated by the implantable device 110.

As stated previously, implantable device 110 includes circuit elements configured to limit an amount of energy that may be outputted by implantable device 110, through one or more electrodes, into the surrounding tissue. Without such circuit elements, the current delivery of the implantable device 110 varies as a function of extraneous situation variables. For examples, when the exciter transmits ultrasonic energy, extraneous situation variables include the ultrasound coupling to the body surface, transducer placement, and applied ultrasonic power. In radiofrequency semi conductor diode based neurostimulation systems, on the other hand, the implant current delivery varies as a function of the applied transmitter power, antenna position, and transmitter coupling to the body surface, for example.

The variation in current delivery due to extraneous situation variables can be overcome by fixing the position of the implant, antenna, coupling methods, and transmit power, and subsequent recalibration to achieve the correct and needed current flow if any of these variables change. However, recalibration is cumbersome and change in output current is undesirable. It would be preferable that the value of neurostimulation be independent of these extraneous situation variables.

Consequently, the implantable device 110 includes circuit elements configured to limit an amount of energy that is outputted by the implantable device 110, through one or more electrodes, into the surrounding tissue. When the output of implantable device 110 is being limited, implantable device 110 is referred to as operating in a saturated mode. In saturation mode, even when the energy output signal 106 of the exciter that is inputted into implantable device 110 is increased, the maximum output of implantable device 110 (e.g., output stimulation 112) remains unchanged. By limiting an amount of energy that may be outputted by implantable device 110, the risk of implantable device 110 transmitting a dangerous amount of energy into a patient's tissue is mitigated. Additionally, when the amount of energy transmitted by exciter 108 into implantable device 110 exceeds that threshold value, it is possible to predict accurately the amount of energy being delivered by implantable device 110, as that amount of energy will be limited to a predetermined value due to the construction of implantable device 110.

Because the output of the implanted device is limited by the implanted device's saturation point, as long as an excess of power is supplied to the implanted device by the external exciter, changes in coupling (as long as they are not excessively severe) will not affect the output voltage of the implanted device—the device will always operate in its saturation mode. Accordingly, in some embodiments, the amplitude of the PWM signal emitted from the external exciter is configured to always place the implanted device into saturated mode. The amount of energy outputted by the implanted device, therefore, is not controlled by varying the amplitude of the excitation signal, but instead by varying the duty cycle of the PWM excitation signal.

The use of an external exciter transmitting PWM excitation signals allows a linear and precise control of the stimulation charge delivered per pulse due to the linear and precise control over the duty cycle. Given certain tissue conductivity conditions (which are generally knowable on a case-by-case basis), there is then a known and controllable current delivered by the neurostimulator implanted device as long as the peak voltage generated by the neurostimulator is saturated at a constant value. Therefore, the total amount of electrical stimulation charge that is transferred to the tissue over the duration of the neurostimulation pulse can be known and controlled by pulse width modulation. Additionally, accurate calibration can be achieved by this method by insuring that the implanted pulse amplitude output is at a known and set value.

This type of current delivery control strategy is applicable to both radiofrequency driven neurostimulators where the electrical source for the implanted device is the rectification of energy from an implanted dipole antenna, as well as in neurostimulation systems based on piezoelectric elements as the energy source for the implanted device, among others.

Figure 2A:
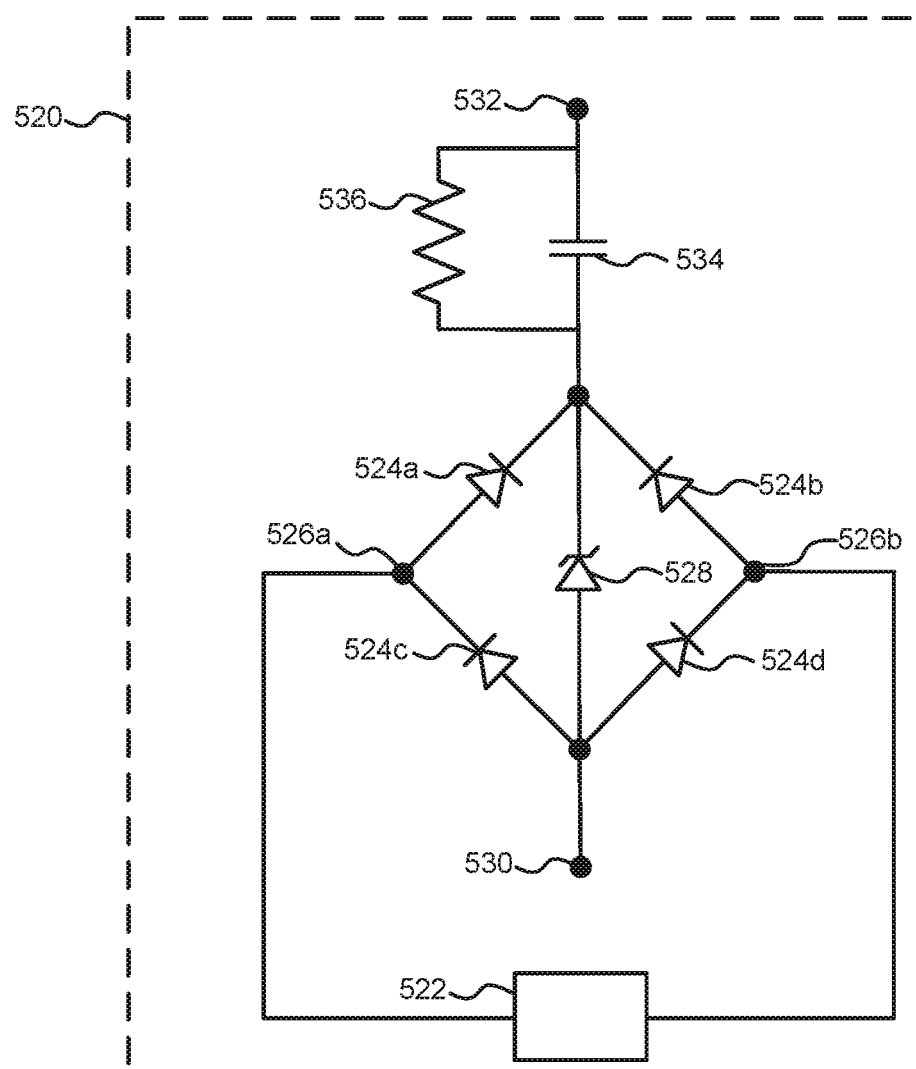
FIG. 2A is a circuit diagram showing an example implementation of an implantable device within the system of FIG. 1.

Referring to FIG. 2A, a circuit diagram illustrates implantable device 520, which is an example implementation of implantable device 110 of FIG. 1 configured to be powered by an ultrasound exciter transmitting a PWM excitation signal. Implantable device 520 includes piezoelectric device 522. Piezoelectric device 522, in response to the application of an ultrasonic signal generated by an exciter, generates a voltage across the device's two terminals. That voltage is then supplied to a voltage rectifier circuit comprising diodes 524a, 524b, 524c, and 524d at nodes 526a and 526b.

Diodes 524a, 524b, 524c, and 524d operate as a rectifier circuit to rectify the alternating output of piezoelectric device 522. Accordingly, when a positive voltage is present at node 526b, diodes 524b and 524c are conductive, while diodes 524a and 524d are not conductive. Conversely, when a positive voltage is present at node 526a, diodes 524a and 524d are conductive, while diodes 524b and 524c are not conductive. Accordingly, the rectifier circuit is configured to cause a current to flow in only a single direction through implantable device 520.

To define a saturation voltage for implantable device 520 (i.e., a maximum output voltage for implantable device 520), implantable device 520 includes a voltage regulator diode 528 connected to the rectifier circuit across the cathodes of diodes 524a and 524b and the anodes of diodes 524c and 524d. In such an arrangement, if the voltage being generated by piezoelectric device 522 should be too great (i.e., the voltage across nodes 526c and 526d exceeds a threshold value), diode 528 is configured to at least partially break down. This reduces the output voltage of the rectifier circuit (diodes 524a, 524b, 524c, and 524d) and sets the output voltage of the rectifier to a value approximately equal to the voltage drop across either diodes 524b and 524c or diodes 524a and 524d of the rectifier circuit. In other words, as diode 528 begins to break down, the low resistance path formed through the breaking-down diode 528 forms a voltage divider with the diodes of the rectifier circuit. This limits the output voltage of the rectifier circuit to a value determined by the voltage drop across diodes 524.

In one implementation of implant device 520, diodes 524a, 524b, 524c, and 524d include Schottky diodes, while diode 528 includes a Zener diode. In that case, the saturation output voltage for implantable device 520 is approximately equal to the breakdown voltage of the Zener diode (e.g., diode 528).

The rectifier circuit (diodes 524a, 524b, 524c, and 524d) of implant device 520 is then connected to electrodes 530 and 532 (e.g., electrodes 114 and 116, respectively, of FIG. 1) for delivering the rectified signal to the tissue surrounding the implanted device. In some cases, capacitor 534 is disposed between rectifier and one of the electrodes of implantable device 520. Capacitor 534 is optional and is configured to allow implantable device 520 to operate as a bi-phasic device wherein some of the energy that is delivered into the tissue surrounding implantable device 520 when implantable device 520 is stimulating (i.e., when there is a voltage across terminals 526a and 526b) is returned from that tissue and stored in capacitor 534 when implantable device 520 is not stimulating. Between stimulating cycles, when implantable device 520 incorporates capacitor 534, leakage resistor 536 may be coupled across to the terminals of capacitor 534 to assist in dissipating energy stored in capacitor 534. By discharging capacitor 534, implantable device 520 can continue to operate in a biphasic mode.

Figure 2B:
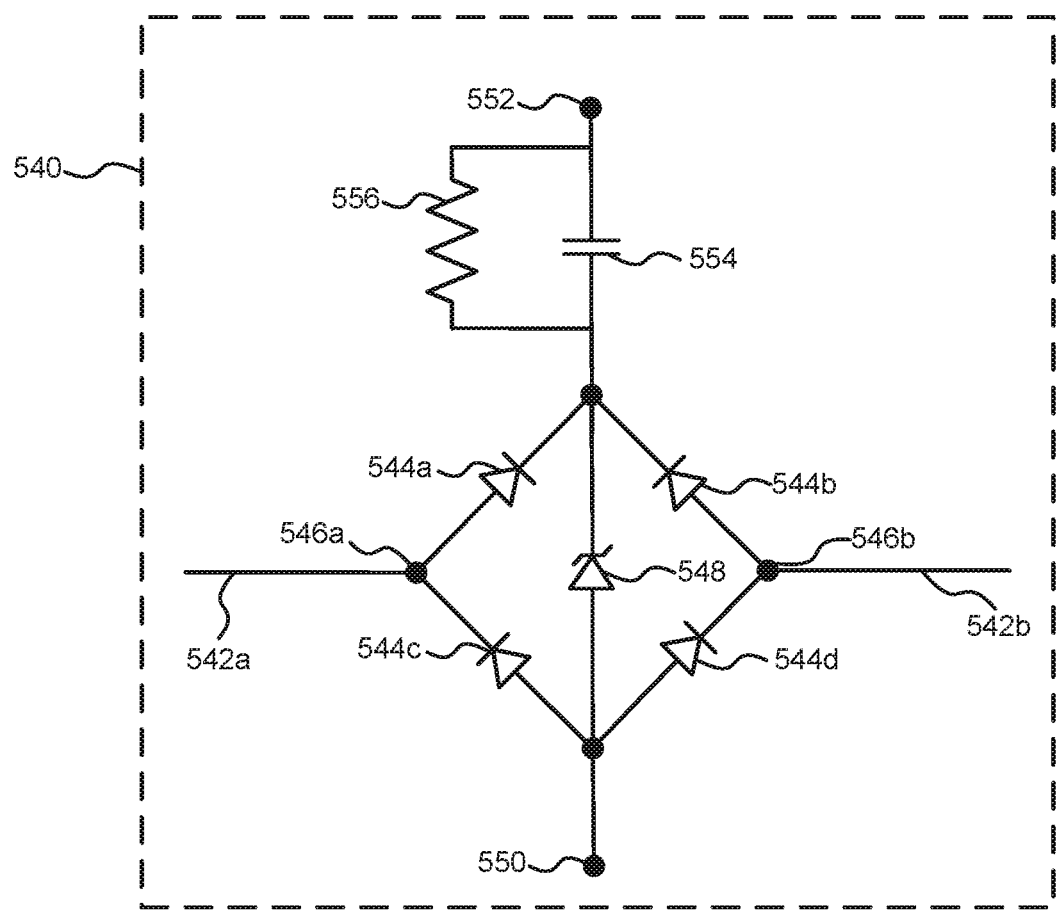
FIG. 2B is a circuit diagram showing an example implementation of implantable device within the system of FIG. 1 configured to be powered by an RF exciter.

FIG. 2B is a circuit diagram showing an example implementation of implanted device 110 of FIG. 1 configured to be powered by an RF exciter transmitting a PWM excitation signal, shown in FIG. 2B as implantable device 540. Implantable device 540 includes dual pole antennas 542a and 542b. Antennas 542, in response to the application of an RF signal generated by an exciter, generate a voltage across nodes 546a and 546b. That voltage is then supplied to a voltage rectifier circuit comprising diodes 544a, 544b, 544c, and 544d at nodes 546a and 546b.

Diodes 544a, 544b, 544c, and 544d operate as a rectifier circuit to rectify the alternating input received from antennas 542. Accordingly, when a positive voltage is present at node 546b, diodes 544b and 544c are conductive, while diodes 544a and 544d are not conductive. Conversely, when a positive voltage is present at node 546a, diodes 544a and 544d are conductive, while diodes 544b and 544c are not conductive. Accordingly, the rectifier circuit is configured to cause a current to flow in only a single direction through implantable device 540. High parasitic capacitance of the shunting diode means it only responds to the DC voltage. The bridge arrangement prevents that capacitance from shorting out the RF antenna.

To define a saturation voltage for implantable device 540 (i.e., a maximum output voltage for implantable device 540), implantable device 540 includes a voltage regulator diode 548 connected to the rectifier circuit across the cathodes of diodes 544a and 544b and the anodes of diodes 544c and 544d. In such an arrangement, if the voltage being generated by antennas 542 should be too great (i.e., the voltage across nodes 546c and 546d exceeds a threshold value), diode 548 is configured to at least partially break down. This reduces the output voltage of the rectifier circuit (diodes 544a, 544b, 544c, and 544d) and sets the output voltage of the rectifier to a value approximately equal to the voltage drop across either diodes 544b and 544c or diodes 544a and 544d of the rectifier circuit. In other words, as diode 548 begins to break down, the low resistance path formed through the breaking-down diode 548 forms a voltage divider with the diodes of the rectifier circuit. This limits the output voltage of the rectifier circuit to a value determined by the voltage drop across diodes 544.

In one implementation of implantable device 540, diodes 544a, 544b, 544c, and 544d include Schottky diodes, while diode 548 includes a Zener diode. In that case, the saturation output voltage for implantable device 540 is approximately equal to the breakdown voltage of the Zender diode (e.g., diode 548).

The rectifier circuit (diodes 544a, 544b, 544c, and 544d) of implantable device 540 is then connected to electrodes 550 and 552 (114 and 116, respectively, of FIG. 1) for delivering the rectified signal to the tissue surrounding the implanted device. In some cases, capacitor 554 is disposed between rectifier and one of the electrodes of implantable device 540. Capacitor 554 is optional and is configured to allow implantable device 540 to operate as a bi-phasic device wherein some of the energy that is delivered into the tissue surrounding implantable device 540 when implantable device 540 is stimulating (i.e., when there is a voltage across terminals 546a and 546b) is returned from that tissue and stored in capacitor 554 when implantable device 540 is not stimulating. Between stimulating cycles, when implantable device 540 incorporates capacitor 554, leakage resistor 556 may be coupled across to the terminals of capacitor 554 to assist in dissipating energy stored in capacitor 554. By discharging capacitor 554, implantable device 540 can continue to operate in a biphasic mode.

In certain implementations of the present system 100, therefore, the maximum amount of power that can be delivered by implantable device 110 into surrounding tissue is determined based upon the characteristics of the voltage or current-limiting device incorporated into implantable device 110 (see, for example, diodes 528 and 548 of implanted devices 520 and 540 of FIGS. 2A and 2B, respectively). By selecting the appropriate value, therefore, the maximum potential energy delivery of implantable device 110 can be controlled, ensuring that the output of implantable device 110 will fall within desired operational criteria.

In certain embodiments, it may be desirable to multiply-up the voltage delivered by the energy acquisition device (e.g., dipole antenna, such as element 542 of FIG. 2B, piezoelectric material, such as element 522 of FIG. 2A, or solar cells) by means of a classic voltage multiplier circuit as known to the art that incorporates multiple diodes and capacitors. Alternately, the output voltage may be multiplied-up by a method of connecting multiple smaller energy acquisition devices, such as piezoelectric elements, in series through diodes such that their individual voltages caused by excitation will sum to a larger voltage. In both cases the strategy is to present higher voltages to the energy limiting devices (e.g., diodes 528 of FIG. 2A or 548 of FIG. 2B) at lower excitation levels so the energy demands placed on the external exciters are not as severe. In some embodiments, the output energy of the implanted device may be alternating-current coupled with an extra series capacitor in the electrode lead, depending on the neural application.

With the maximum output of implantable device 110 being controlled by the voltage or current-limiting device incorporated therein, exciter 108 is then configured to output a signal configured to control how much energy is outputted by implantable device 110 into the surrounding tissue. In the present implementation, exciter 108 generates a PWM output signal. The magnitude of the signal outputted by exciter 108 is selected to provide an excess of energy to implantable device 110. As such, when exciter 108 is transmitting, the outputted signal causes the energy acquisition device within implantable device 110 to generate an output voltage that exceeds the maximum as set by the voltage or current-limiting device contained within implantable device 110—implantable device 110 operates in its saturation mode. In order to reduce the amount of energy being output by implantable device 110, therefore, the duty cycle of the PWM signal outputted by exciter 108 is reduced. This reduces an amount of energy being transmitted to implantable device 110, reducing an amount of energy being output by implantable device 110 by a corresponding, and well defined, amount.

The PWM excitation signal transmitted by the external exciter comprises modulated pulses or subpulses that are relatively short and high frequency (e.g., 50-100 kHz and 5-10 microsec in duration) compared to the desired stimulation pulse. By adjusting the duration of these modulated pulses, the total charge delivered per neurostimulation pulse can be adjusted, thereby modulating the physiologic response. However, because the individual modulated pulses are of sufficiently short duration (e.g., 5 microseconds), excitable tissues of the body cannot respond to the shorter modulated pulses, but will respond to a train of short, modulated pulses, if the train is of sufficient length (e.g., on the order of hundreds of microsecond to milliseconds).

High frequency excitation chopping at a period of 5-10 microseconds, creates subpulses within the, for example, 500 microsecond desired stimulation signal. This chopping can be effected so that it is a variable duty cycle pulse waveform and so the on-time can be accurately controlled.

In the specific case of the ultrasound pulse delivery, the subpulse widths of the desired stimulation signal are typically fixed by the acoustic frequency of the ultrasound transducer and so are usually on the order of 0.5 microseconds to 5 microseconds. In this case the pulse width duty cycling is achieved by varying their repetition rate within a burst that constitutes the longer duration of the desired stimulation pulse.

Figure 3A:
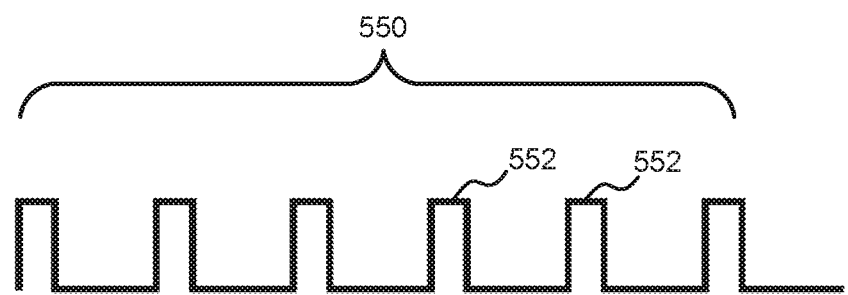
FIGS. 3A and 3B, are each a schematic showing a pulse that is made up of a number of respective subpulses.
Figure 3B:
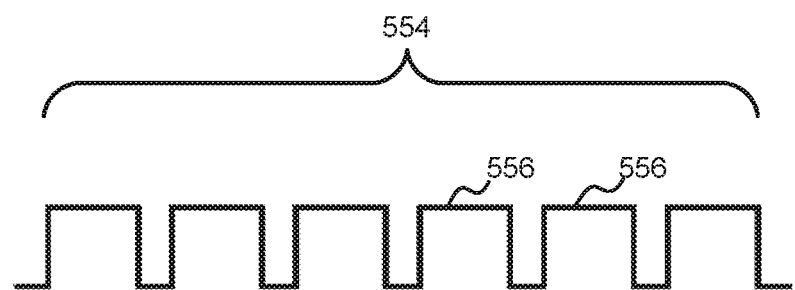

FIGS. 3A and 3B are example pulse width modulated neurostimulation signals that are transmitted by the exciter 108 to an implantable device 110. FIG. 3A shows a first pulse 550 that is made up of a number of subpulses 552. FIG. 3B shows a second pulse 554 made up of a number of subpulses 556. Although the magnitude of each subpulse of pulses 550 and 554 are the same, it can be seen that the duration of the subpulses in pulse 550 are of a shorter duration that the subpulses in pulse 554. Accordingly, the duty cycle of pulse 550 is less than the duty cycle of pulse 554. As a result, pulse 550 is arranged to transmit less energy into an implanted device than pulse 554. In one implementation, each of pulses 550 and 554 have a duration of between approximately 500 microseconds and 10 milliseconds.

By varying the duty cycle of the neurostimulating pulses transmitted by an exciter into the implanted device, the exciter can control an amount of energy that the implanted device transmits into its surrounding tissue.

Because the present exemplary system calls for the energy transmitted by exciter 108 to 'saturate' the output of implantable device 110, and only reduces the energy generated by implantable device 110 by reducing the duty cycle of the outputted PWM signal, the present exemplary system allows for the energy being output by implantable device 110 to be well controlled. Because the system is saturated, even relatively poor coupling between exciter 108 and implantable device 110 does not greatly affect the amount of energy outputted by implantable device 110 (unless the poor coupling is so severe as to cause exciter 108 to be unable to communicate enough energy to implantable device 110 so that implantable device 110 can be saturated).

Although the PWM signal outputted by exciter 108 can result in the signal outputted by the energy acquisition device of implantable device 110 to include a number of subpulses, those subpulses are filtered or smoothed by the electrical capacitance present within the voltage or current-limiting device, as well as capacitance of the electrode within implantable device 110, the electrode-tissue connection, and the tissue itself. Due to that smoothing, the resulting neurostimulation pulse waveform outputted by the implanted device is smoothed and resembles that of a typical neurostimulation pulse from a conventional generator but whose amplitude is continuously variable. Accordingly, the pulse ultimately transmitted from implantable device 110 into the surrounding tissue is relatively smooth, as compared to the PWM signal outputted by exciter 108 and received, initially, by implantable device 110.

In other implementations of the system, exciter 108 and the energy acquisition device of implantable device 110 can be replaced by other systems for wirelessly communicating energy from an external device to an implanted device. For example, exciter 108 may include an optical exciter that communicates energy into an implant that includes a number of p-n junction diodes as energy receives. In that case, the exciter illuminates the implanted device using transillumination of tissue in order to communicate energy thereto.

Figure 4:
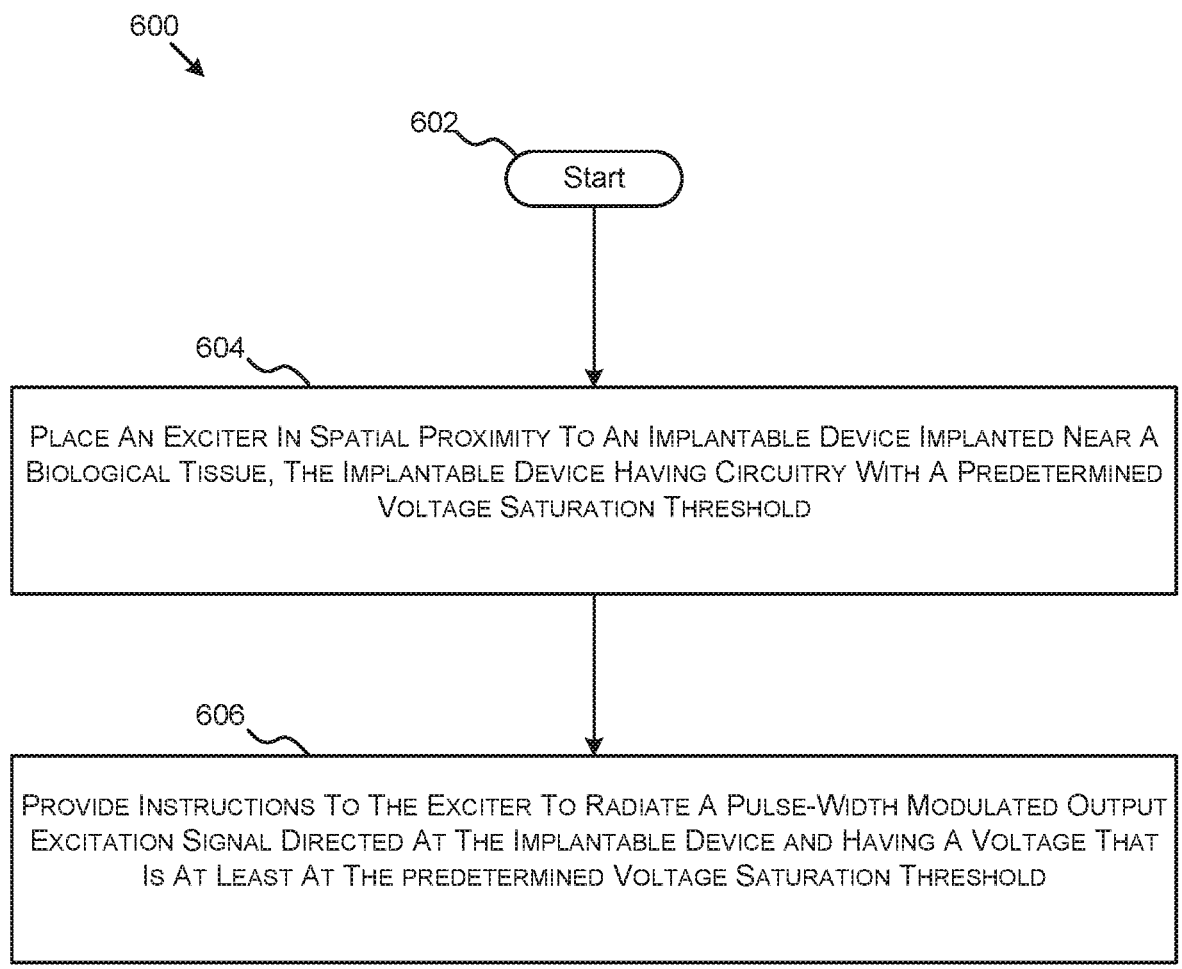
FIG. 4 illustrates a flow chart of an exemplary method for neurostimulation using the neurostimulation system of FIG. 1.

Referring to FIG. 4, a flow chart illustrates an exemplary method 600 for neurostimulation. Method 600 starts at step 602 and proceeds to step 604. At step 604, the exciter 108 is placed in spatial proximity to the implantable device 110 that is implanted near biological tissue, such as near a nerve of a subject. To illustrate, the exciter 108 is placed upon the epidermis of the subject's neck, proximate to the implantable device 110 that is implanted near the subject's vagus nerve. The implantable device 110 has circuitry with a predetermined saturation threshold, as previously described. At step 606, instructions are provided to the exciter 108 to create a pulse-width modulated output signal 106 directed at the implantable device 110. Here, the voltage level of the output signal 106 is at least at the predetermined saturation threshold of the implantable device 110.

The schematic flow chart diagrams included are generally set forth as a logical flow-chart diagram (e.g., FIG. 4). As such, the depicted order and labeled steps are indicative of one embodiment of the presented method. In certain embodiments, other steps and methods are conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types are employed in the flow-chart diagrams, they are understood not to limit the scope of the corresponding method (e.g., FIG. 4). Indeed, some arrows or other connectors may be used to indicate only the logical flow of the method. For instance, an arrow indicates a waiting or monitoring period of unspecified duration between enumerated steps of the depicted method. Additionally, the order in which a particular method occurs may or may not strictly adhere to the order of the corresponding steps shown.

In certain embodiments, individual steps recited in FIG. 4 are combined, eliminated, or reordered. In certain embodiments, a computer readable program code resides on a tangible computer-readable medium, where that computer readable program code can be executed by a computer external to, or internal to, system 100 (FIG. 1), to perform one or more of steps recited herein. In either case, in certain embodiments, the computer readable program code is encoded in a non-transitory computer readable medium comprising, for example, a magnetic information storage medium, an optical information storage medium, an electronic information storage medium, and the like. "Electronic storage media," means, for example and without limitation, one or more devices, such as and without limitation, a PROM, EPROM, EEPROM, Flash PROM, compactflash, smartmedia, and the like.

Examples of computer readable program code include, but are not limited to, micro-code or micro-instructions, machine instructions, such as produced by a compiler, code used to produce a web service, and files containing higher-level instructions that are executed by a computer using an interpreter. For example, embodiments are be implemented using Java, C++, or other programming languages (e.g., object-oriented programming languages) and development tools. Additional examples of computer code include, but are not limited to, control signals, encrypted code, and compressed code.

While various embodiments have been described above, it should be understood that they have been presented by way of example only, not limitation, and various changes in form and details may be made. Any portion of the apparatus and/or methods, for example, described herein may be combined in any combination, except mutually exclusive combinations. The embodiments described herein can include various combinations and/or sub-combinations of the functions, components and/or features of the different embodiments described. For example, multiple, distributed qualification processing systems can be configured to operate in parallel.

Figure 5A:
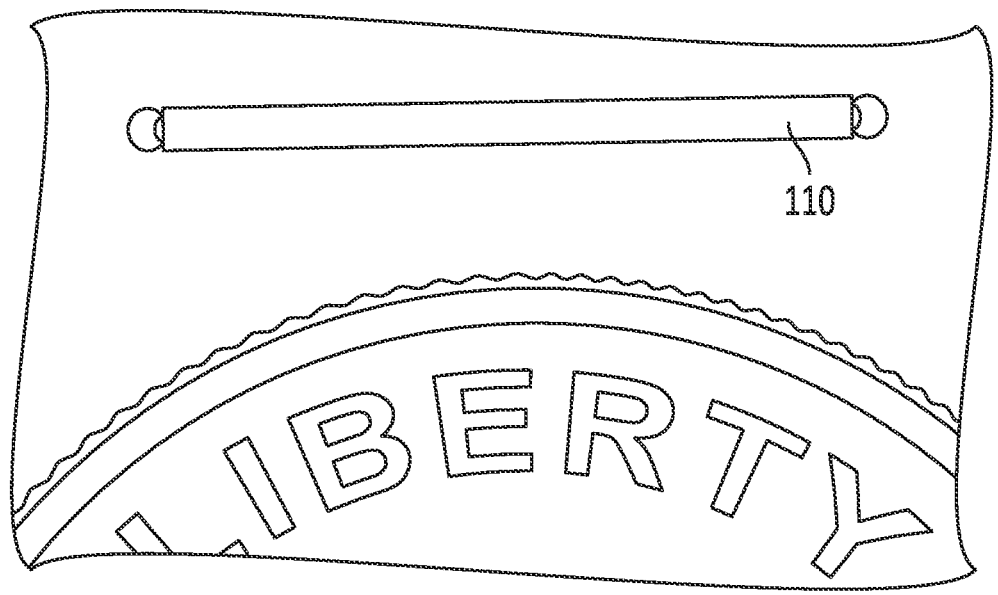
FIGS. 5A and 5B are illustrations showing example implanted devices.
Figure 5B:
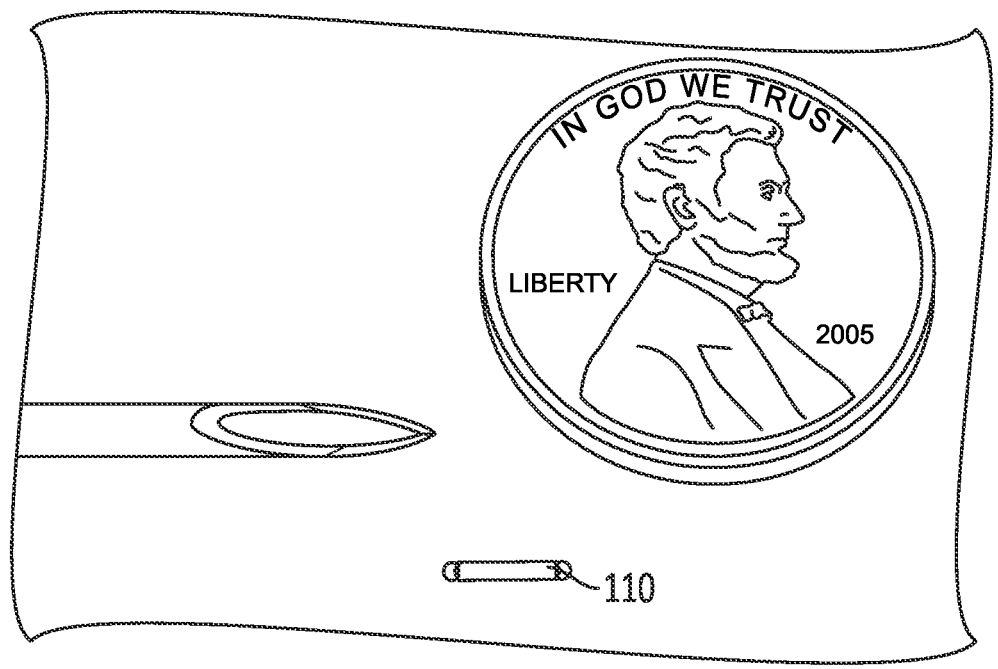

FIGS. 5A and 5B are photographs showing example implanted devices 110. In FIG. 5A, an implantable device 110 is placed next to a U.S. quarter ($0.25 coin), which shows the relative size of the implantable device. In FIG. 5B, an implantable device 110 is placed next to a U.S. penny ($0.01 coin) and the tip of a needle, which shows the relative size and ability to insert the implantable device 110 using a syringe and needle.

Figure 6:
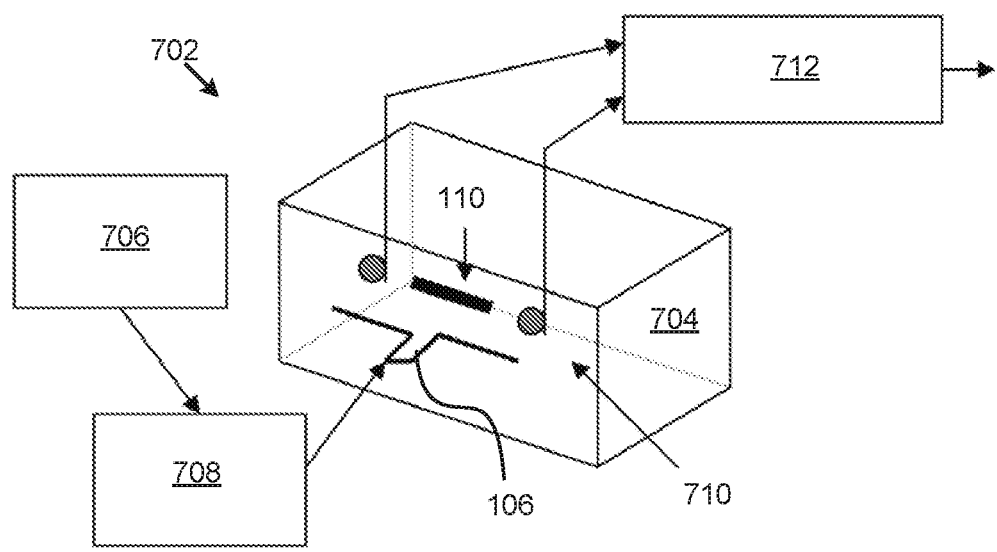
FIG. 6 is a schematic diagram showing a test setup for a neurostimulation system.

FIG. 6 is a schematic diagram showing a test setup 702 for a neurostimulation system. In this setup, an implantable device 110 is placed in a saline solution 704. A pulse controller 706 provides electrical signals to an RF generator 708. In one embodiment, the RF generator 708 may be a 915 MHz generator. The RF generator radiates an RF signal that provides an output signal 106 to the implantable device 110. The implantable device can provide neurostimulation signals that can be picked up by test electrodes 710. In one example, the test electrodes may be Ag/AgCl pickups. Finally, the test setup 702 may use a signal receiver 712 to measure the amount of stimulation current produced by the implantable device 110. In some embodiments, the signal receiver 712 may include a differential amplifier and a low-pass filter In some embodiments, it is useful in achievement of neurostimulator current regulation that the implant output voltage pulses be of a constant value and changed only in their width or duty cycle in order to determine average current delivered to the tissue. Using the present system, the constancy of this voltage value is achieved by driving the implant 110 to an electrical saturation whereby the electrode output voltage is determined by the characteristics of a Zener diode, or other current or voltage-limiting device, as described above. However the exciter power level at which this saturation occurs cannot be directly determined leading to an uncertainty of how much power to use. Although operational characteristics of the system, such as its response to coupling changes will give insight into this issue it is possible to determine or estimate the level of exciter power.

In some embodiments, the present system uses a method of detecting the re-radiated RF emissions of the implant as an indicator of its electrical operation. In specific, a nearby radiofrequency receiver 713 coupled to the surface of the body, by way of a close-coupled antenna or by skin surface electrodes, is tuned to the second harmonic of the implant excitation frequency. The harmonic emission is detectable because the implant 110 re-radiates a distorted RF signal compared to its excitation. The distortion and harmonic generation is due to the nonlinear voltage threshold behavior of the diode system. The second harmonic is particularly strong and passes out from the implant and through the tissue to the local receiver.

The present system extends this capability to use implanted diode harmonic emissions to allow the determination of the actual current flow in tissue. The first through third radiofrequency harmonics of the fundamental drive frequency that may be re-emitted from a diode system are detected and recorded as a function of a linear ramp or staircase step up in exciter power. The specific received amplitudes of the harmonics as they increase with exciter power have different rising shapes and characteristics that are unique to the variables of a given current flow, stimulating electrode load impedance, and any electrode or system offset voltages. Thus through the use of a look-up table, curve fitting, or other methods of pattern recognition known to the art the variables can be uniquely determined.

For detecting the second harmonic, and in the case of a radiofrequency excited device 708 at 915 MHz, an RF receiver 712 would be tuned to 1830 MHz. In the case of an ultrasound excited device at 1 MHz for example, a local radio receiver would be tuned to 2 MHz.

Using this arrangement, it is possible to find that when the amplitude of the second harmonic is saturated at its highest amplitude then we know that the implant electrode voltages are also saturated at their highest voltage and a satisfactory operating point has been achieved with exciter power. This operating point can be detected by ramping up the excitation power level to the implant to the point where the amplitude of the received second harmonic no longer increases. This becomes a reference point of the exciter power level. It would then be possible to set the exciter to that specific level or higher to achieve a working margin of safety.

In the specific case of ultrasound excited neurostimulators another method of receiving the neurostimulator RF return signal is possible. The exciter 110 launches ultrasound pulses short enough, 1-5 microseconds in duration, such that the tissue path acoustic transit time delay allows separation of the RF artifact accompanying the excitation of the ultrasound transducer from the received signal. This means that the implant generates an electrical response in tissue with a multiple microsecond order delay relative to the launched excitation pulse. In this case the receiver can be gated on with a delay relative to the launched pulse such it rejects the transmit burst artifact and directly detects the resulting implant pulse current in tissue by way of body surface electrodes for signal pickup or by way of a close coupled antenna. Examination of the rise in the detected signal amplitude relative to the exciter drive similarly gives an indication of implant output pulse amplitude saturation and hence operating point determination is possible. Gradation in implant power output is achieved by varying the repetition rate only of the fixed width ultrasound pulses.

In some embodiments, the exciter 110 power is increased by 20% or some chosen margin over the point at which the exciter 110 is operating in saturation mode to ensure that power coupling changes to the implant over this chosen range do not affect the amplitude of output pulses of the implant and that pulse width modulation is the regulator of implant current delivery.

Most battery-powered wireless nerve- and muscle-stimulators have onboard current control. This digital circuitry can limit the minimum size and power, and add cost for custom animal-specific stimulators. Control is needed for batteryless implants because the power link efficiency can change with body movement, for any wireless modality (induction, infrared, volume conduction).

The setup in FIG. 6 models an interrogator to find the DC current though an implantable device 110, using backscattered harmonics of the AC drive. The interrogator works regardless of changes in power loss, electrode resistance, and signal loss. The implantable device 110 may be calibrated by a series of probe inputs, then driven at a known current.

To find link efficiency and electrode resistance, the interrogator drives the implantable device 110 at several relative AC voltages and observes the harmonics. Absolute voltages are unknown due to power loss, and harmonics must be normalized to cancel out the return signal loss (assumed to be linear). The harmonics are compared to a lookup table, which has harmonics at known drives—the closest match gives the estimated AC voltage and resistance. Net error of this estimation is modeled by trying to drive a given current using the estimated loss and resistance, rather than the true loss and resistance.

Given a received signal with 20 dB SNR (adding a random 1% variance across the harmonics), the interrogator calculates with over 10 dB accuracy (less than 10% variance in current) the drive needed for a 100 uA DC current. For a Schottky diode, this holds above 100 mV and 500 ohms. Below, accuracy worsens due to low harmonics.

This interrogator is able to measure enough information to find the unknowns: harmonics are unique across drive and resistance. The model does not yet study variables like capacitance, which change harmonics over time and frequency.

One possible use is to control an ultrasound-powered nerve stimulator. Power is sent from a transducer on the skin to a piezoelectric implant. A diode rectifies the MHz electrical current from the piezoelectric implant; this current stimulates the nerve. MHz harmonics on the stimulation current can be seen by skin electrodes. The interrogator would send a set of short pulses to find the power loss and resistance, then calculate a pulse to drive the desired current.

A diode can also be used as a simple impedance or biopotential sensor—the interrogator can find the resistance or a DC electrode bias, calculated from the AC harmonics.

Figure 7A:
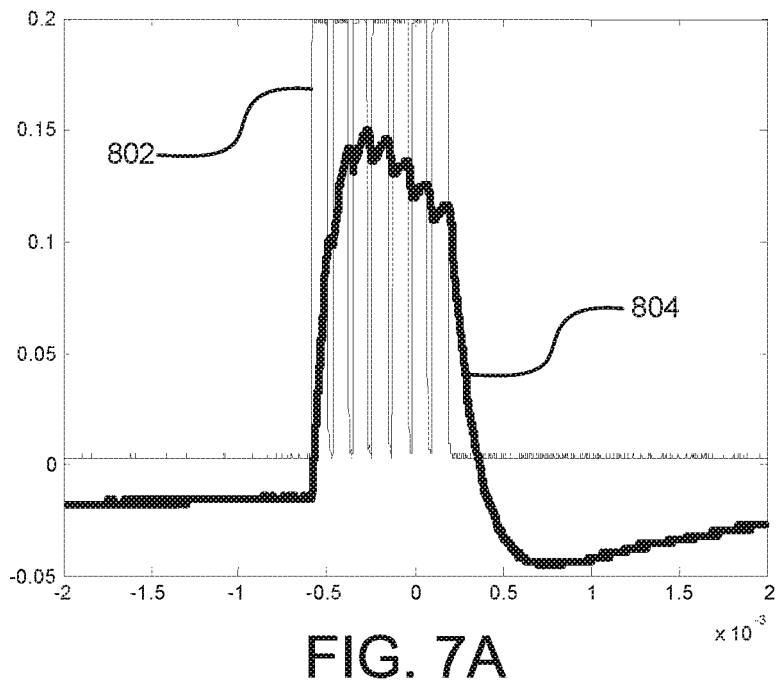
FIGS. 7A-7C are oscilloscope outputs showing waveforms for pulses having subpulses of varying duty cycles.
Figure 7B:
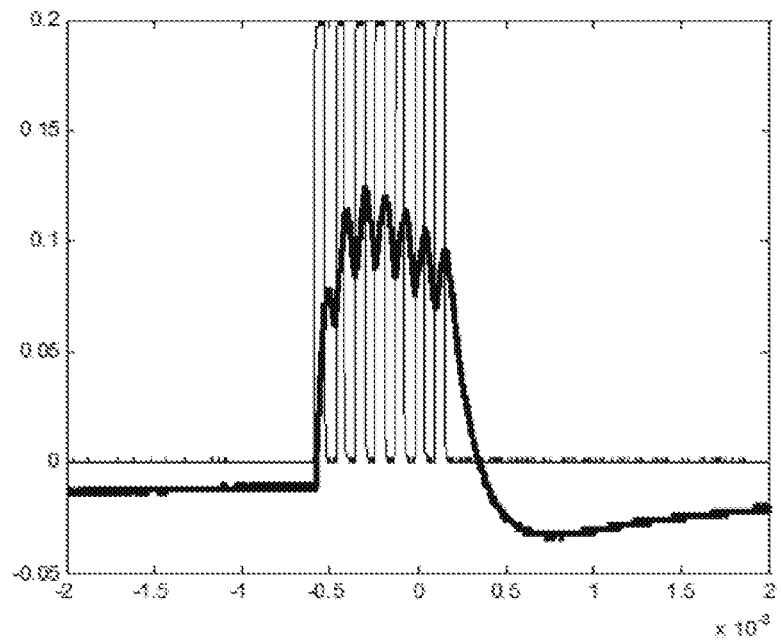
Figure 7C:
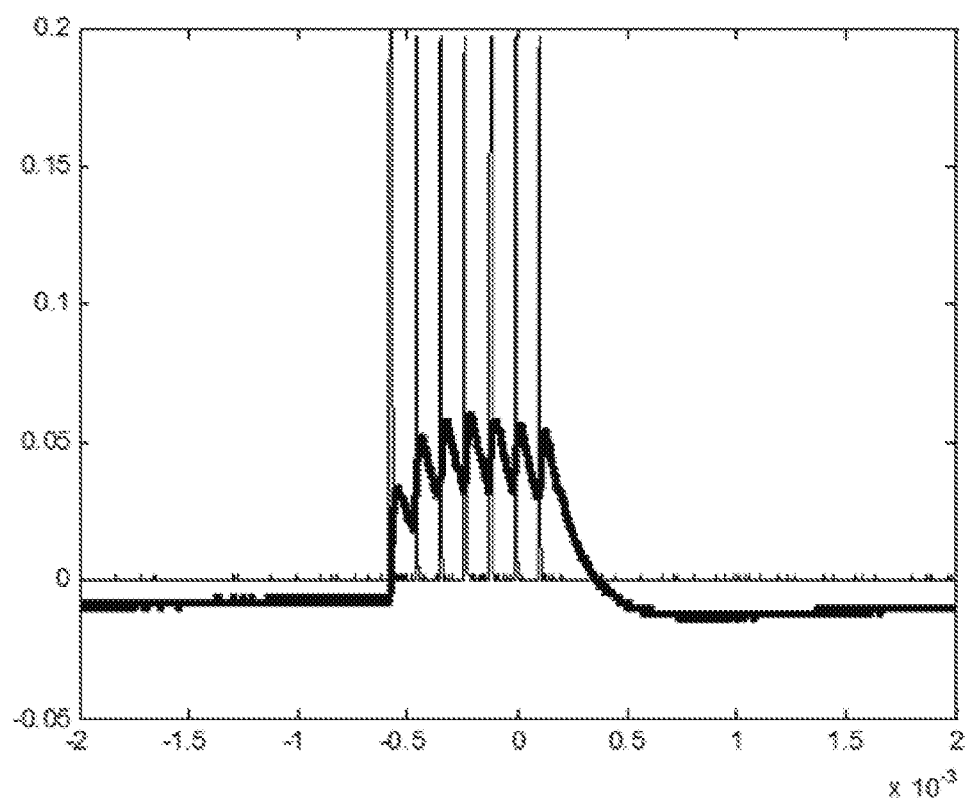

FIGS. 7A-7C show examples of the current that can be delivered by an implantable device 110. In these examples, an RF implantable device receives RF signals 802. When the RF signal 802 is chopped at an appropriately fast rate (above ~50 kHz, below ~1 MHz), the neuron will not respond to individual pulses but rather to the group as would a low pass filter. The plots show the effect of using different pulse widths in a train of seven pulses having a burst duration of 1 ms on the resulting detected potential driven in solution by the implantable device 110. The thin trace shows the pulse control signal from the function generator that amplitude modulates the RF pulse 802. The thick trace shows stimulation current 804 in solution resulting from the implantable device 110. FIG. 7A shows a pulse control signal 802 having a 90% duty cycle. FIG. 7B shows a pulse control signal having a 50% duty cycle. FIG. 7C shows a pulse control signal having a 10% duty cycle. As can be seen from the plots, the lower the duty cycle, the lower the amount of stimulation current that is delivered to the tissue.

Figure 8:
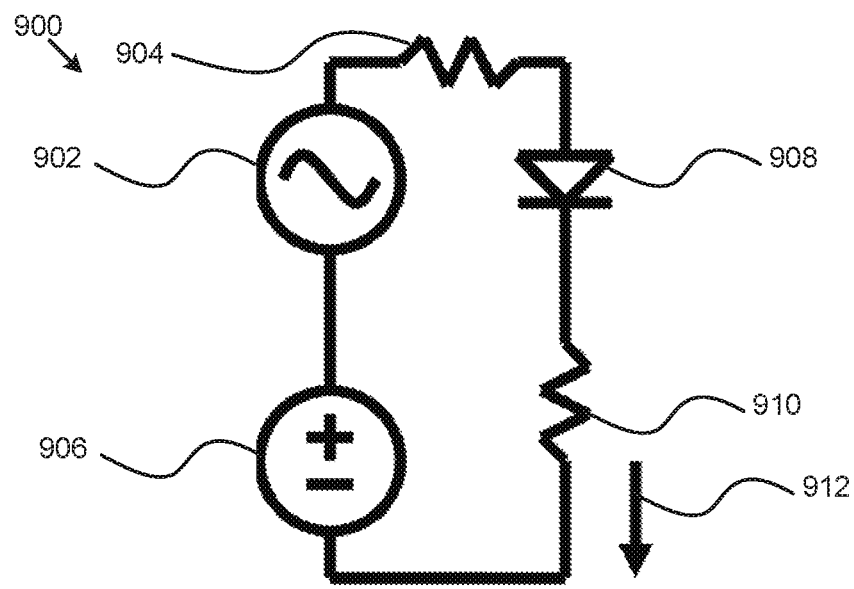
FIG. 8 is a schematic diagram of a model circuit for neurostimulation.

FIG. 8 shows a simplified schematic diagram of a circuit 900 having a single rectifying diode (half-wave rectifier). Although the following describes methods for calculating the electrical characteristics of an implanted device 110 having a half-wave rectifier, the same concepts are applicable to devices implementing a full-wave rectifier as described above.

The circuit 900 includes an RF generator 902 that produces and RF signal as described above. In addition, the circuit 900 has a source impedance 904, a rectifier 908, and offset 906, and a load impedance 910. Although the signal generated by the RF generator 902 and the source impedance may be known, the offset voltage 906 load impedance 910 and resulting neurostimulation current 912 may not be known. In addition, the maximum RF signal that causes the rectifier 908 to become saturated may not be known. However, using the methods described herein, the load impedence (Rload), offset voltage (V_bias_offset), and maximum RF signal that causes saturation (V_RF_max) may be determined even though there may be many variables, such as a change in RF coupling and tissue electrical characteristics.

Figure 9:
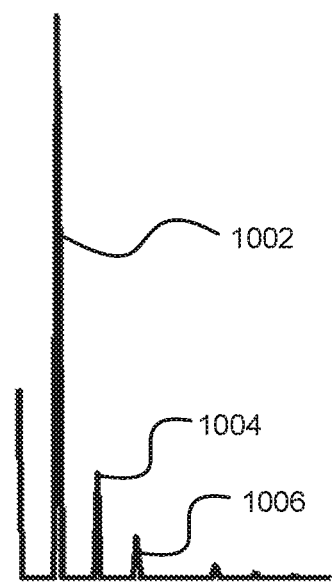
FIG. 9 shows the spectrum of the current generated in the circuit of FIG. 8.

FIG. 9 shows the spectrum of the current generated in the circuit of FIG. 8. Because the rectifier rectifies the voltage that is produced by the RF generator 902, the spectrum includes several harmonics. As seen in FIG. 9, the first harmonic 1002 has the largest amplitude, followed by the second harmonic 1004. The third harmonic 1006 has an even lower amplitude. Although there may be more harmonics that could potentially be measured, in many cases the first three harmonics are the easiest to measure and can have sufficient information to determine the load impedance, bias offset and max RF signal for the example circuit in FIG. 8.

In the described method, the peaks of the $1^{st}$ (1002), $2^{nd}$ (1004), and $3^{rd}$ (1006 harmonics are extracted and plotted against the RF drive voltage of the RF generator 902. The curve may be produced for a power range of RF signal from 10% to 100% of the maximum RF drive. Because the signal loss may vary differently for different harmonics, they must be normalized separately to cancel that unknown.

Figure 10A:
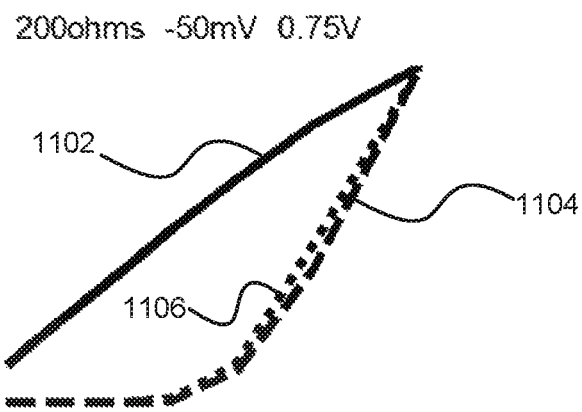
FIGS. 10A-B show plots of neurostimulation signals and harmonics of same for different configurations of the model circuit of FIG. 8.

FIG. 10A shows one example of a plot where the load impedance 910 is known to be 200 ohms, the offset 906 is known to be −50 mV, and the maximum RF signal is 0.75V. The plot in FIG. 10A shows the normalized amplitudes of the first harmonic 1102, the second harmonic 1104, and the third harmonic 1106.

Figure 10B:
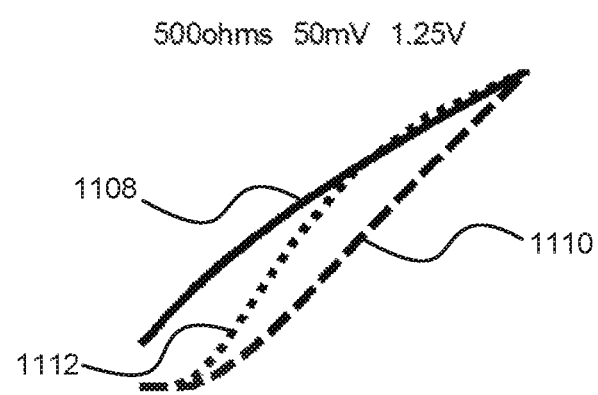

FIG. 10B shows a plot where the load impedance 910 is known to be 500 ohms, the offset 906 is known to be 50 mV, and the maximum RF signal is 1.25V. The plot in FIG. 10B shows the normalized amplitudes of the first harmonic 1108, the second harmonic 1110, and the third harmonic 1112.

Using many measurements such as those described above in connection with FIGS. 10A-B, a look-up table can be assembled that characterizes many different situations with varying load impedances, offset voltages and maximum RF signals. Using that lookup table, it is possible to characterize an implanted device 110 that resides inside a patient's body, which can be useful for applying the appropriate about of stimulation signal to produce a desired amount of neurostimulation or to ensure that an implanted device is operating in a saturation mode as described above.

Figure 11:
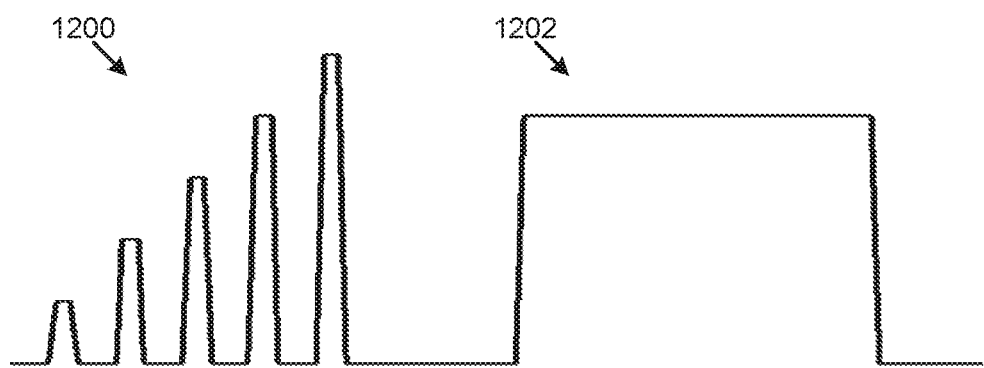
FIG. 11 shows a method for calibrating and implementing a neurostimulator in a human or animal.

FIG. 11 shows how the methods described above may be implemented in a human or animal. Initially, a short train of probe pulses 1200 can calibrate the system as described above. Subsequently, a stimulation pulse 1202 is driven using the characteristics that were determined as described above. This method assumes that any losses or characteristics of the implant remain constant over the whole period of neurostimulation. However, additional calibrations may be made to compensate for variations, including calibrations that are conducted while performing neurostimulation.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

The invention claimed is:

1. A neurostimulation system for stimulating tissue, the system comprising:
   an implantable device, the implantable device comprising:
      an energy acquisition device configured to wirelessly receive an excitation signal and including a device selected from the group consisting of a piezoelectric element configured to wirelessly receive the excitation signal, a dipole antenna configured to wirelessly receive the excitation signal, and a solar cell configured to wirelessly receive the excitation signal;
      an electrode configured to deliver an electric current to the tissue, the electric current being powered directly by the excitation signal; and
      a rectifier connected to the energy acquisition device and configured to rectify an AC electric current, received from the energy acquisition device, to a DC electric current.

2. The neurostimulation system of claim 1, further comprising an exciter configured to radiate the excitation signal as a pulse width modulated excitation signal to the energy acquisition device.

3. The neurostimulation system of claim 2, wherein the implantable device further comprises
   a voltage-limiting device, directly connected to the rectifier,
   wherein the rectifier is directly connected to the energy acquisition device, and
   wherein the electrode is directly connected to the voltage-limiting device.

4. The neurostimulation system of claim 3, wherein the rectifier includes a Schottky diode.

5. The neurostimulation system of claim 3, wherein a pulse of the pulse width modulated excitation signal has an amplitude sufficient to cause the implantable device to operate in a voltage saturation mode.

6. The neurostimulation system of claim 2,
   wherein the energy acquisition device is configured to convert the excitation signal into the AC electric current, and
   wherein the electrode is configured to deliver at least a portion of the DC electric current to the tissue.

7. The neurostimulation system of claim 1,
   wherein the implantable device is capable of fitting within a lumen of a hypodermic needle.

8. The neurostimulation system of claim 7, further comprising an exciter configured to radiate the excitation signal as a pulse width modulated excitation signal to the energy acquisition device.

9. The neurostimulation system of claim 8, wherein the implantable device has a length of at least 1 cm and at most 2 cm.

10. The neurostimulation system of claim 8, wherein the implantable device further comprises
a voltage-limiting device configured to limit an amount of energy delivered to the tissue.

11. The neurostimulation system of claim 10, wherein the rectifier includes a Schottky diode.

12. The neurostimulation system of claim 8, wherein:
the electrode is a first electrode,
the implantable device further comprises a second electrode configured to deliver an electric current to the tissue,
the first electrode is at a first end of the implantable device, and
the second electrode is at a second end of the implantable device.

13. The neurostimulation system of claim 1, wherein the implantable device is configured so that power received at the energy acquisition device from the excitation signal is provided immediately to the electrode.

14. The neurostimulation system of claim 1, wherein the excitation signal includes an ultrasound signal, and
wherein the energy acquisition device includes a piezoelectric element including a piezoelectric material and configured, when the implantable device is implanted within the tissue, for the piezoelectric material to wirelessly receive the ultrasound signal from the tissue and for the piezoelectric material to generate a voltage when the ultrasound signal is wirelessly received by the piezoelectric material.

15. The neurostimulation system of claim 1, wherein the energy acquisition device includes a dipole antenna configured to wirelessly receive the excitation signal.

16. The neurostimulation system of claim 1, wherein the energy acquisition device includes a solar cell configured to wirelessly receive the excitation signal.

17. A neurostimulation system for stimulating tissue, the system comprising:
an implantable device, the implantable device comprising:
an energy acquisition device configured to wirelessly receive an excitation signal;
an electrode configured to deliver an electric current to the tissue, the electric current being powered directly by the excitation signal; and
a rectifier connected to the energy acquisition device and configured to rectify an AC electric current, received from the energy acquisition device, to a DC electric current,
wherein the implantable device is configured, upon receipt of the excitation signal having power in a first harmonic, to re-radiate a portion of the received excitation signal in a re-radiated signal having power in an nth harmonic, n being an integer greater than 1.

18. The neurostimulation system of claim 17, further comprising an exciter configured to radiate the excitation signal to the energy acquisition device.

19. The neurostimulation system of claim 18, wherein the excitation signal is a pulse width modulated signal.

20. The neurostimulation system of claim 18, further comprising a receiver configured to detect the nth harmonic of the re-radiated signal.

21. The neurostimulation system of claim 20, wherein the nth harmonic is the second harmonic.

22. A method for performing neurostimulation of the tissue of a subject using the neurostimulation system of claim 20, the method comprising:
radiating, by the exciter, the excitation signal to the energy acquisition device;
detecting, by the receiver, the nth harmonic of the re-radiated signal; and
increasing the power of the excitation signal until an amplitude of the detected nth harmonic no longer increases.

23. The neurostimulation system of claim 18, wherein the implantable device further comprises
a voltage-limiting device configured to limit an amount of energy delivered to the tissue, and
wherein the rectifier includes a Schottky diode.

24. A neurostimulation system for stimulating tissue, the system comprising:
an implantable device, the implantable device comprising:
an energy acquisition device configured to wirelessly receive an excitation signal;
an electrode configured to deliver an electric current to the tissue, the electric current being powered directly by the excitation signal; and
a rectifier connected to the energy acquisition device and configured to rectify an AC electric current, received from the energy acquisition device, to a DC electric current; and
an exciter configured to radiate the excitation signal as a pulse width modulated excitation signal to the energy acquisition device, a pulse of the pulse width modulated excitation signal having an amplitude sufficient to cause the implantable device to operate in a voltage saturation mode in which the power output by the implantable device in response to the pulse width modulated excitation signal is the same as the power that would be output by the implantable device in response to a higher-power pulse width modulation excitation signal.

* * * * *